United States Patent [19]

Abercrombie

[11] Patent Number: 5,346,698
[45] Date of Patent: * Sep. 13, 1994

[54] SYNERGISTIC PESTICIDAL COMPOSITIONS

[75] Inventor: Kenneth D. Abercrombie, Clovis, Calif.

[73] Assignee: Mycogen Corporation, San Diego, Calif.

[*] Notice: The portion of the term of this patent subsequent to Mar. 9, 2010 has been disclaimed.

[21] Appl. No.: 28,041

[22] Filed: Mar. 8, 1993

Related U.S. Application Data

[63] Continuation-in-part of Ser. No. 641,419, Jan. 15, 1991, Pat. No. 5,192,546.

[51] Int. Cl.$^5$ .............................. A01N 25/00
[52] U.S. Cl. .................... 424/405; 514/30; 514/53; 514/68; 514/69; 514/450
[58] Field of Search ............ 424/405; 514/30, 53, 514/450, 68, 69

[56] References Cited

U.S. PATENT DOCUMENTS 4,310,519  1/1982  Albers-Schonberg et al. ...... 514/30
4,560,677  12/1985  Dybas ................................. 514/30

FOREIGN PATENT DOCUMENTS 0094779  8/1983  European Pat. Off. .
0125155  4/1984  European Pat. Off. .

OTHER PUBLICATIONS

Anderson, T. E., J. R. Babu, R. A. Dybas, and H. Mehta (1986) "Avermectin B$_1$: Ingestion and Contact Toxicity Against *Spodoptera eridania* and *Heliothis virescens* (Lepidoptera: Noctuidae) and Potentiation by Oil and Piperonyl Butoxide" Journal of Economic Entomology 79(1):197–201.

Burg, Richard W. et al. (1979) "Avermectins, New Family of Potent Anthelmintic Agents: Producing Organisms and Fermentation" Antimicrobial Agents and Chemotherapy 15(3):361–367.

Boyce Thompson Institue for Plant Research 58th Annual Report (1981) pp 1–44.

*Primary Examiner*—Thurman K. Page
*Assistant Examiner*—Robert H. Harrison
*Attorney, Agent, or Firm*—Saliwanchik & Saliwanchik

[57] ABSTRACT

Described and claimed are methods and compositions for the control of pests. According to the subject invention, a fatty acid or mixture of fatty acids can be combined with one or more avermectins or related compounds to achieve synergistic control of pests.

30 Claims, No Drawings

SYNERGISTIC PESTICIDAL COMPOSITIONS

CROSS-REFERENCE TO A RELATED APPLICATION

This is a continuation-in-part of pending application Ser. No. 07/641,419, filed Jan. 15, 1991, now U.S. Pat. No. 5,192,546.

BACKGROUND OF THE INVENTION

Insects and other pests cost farmers billions of dollars annually in crop losses and in the expense of keeping these pests under control. The losses caused by pests in agricultural production environments include decrease in crop yield, reduced crop quality, and increased harvesting costs.

Chemical pesticides have provided an effective method of pest control; however, the public has become concerned about the amount of residual chemicals which might be found in food, ground water, and the environment. Stringent new restrictions on the use of pesticides and the elimination of some effective pesticides from the market place could limit economical and effective options for controlling costly pests.

There is a great need for novel pest control methods which reduce the amount of pesticides necessary to obtain acceptable levels of control. Researchers have experimented with various combinations of chemicals as one approach to identify compositions which have desirable pesticidal characteristics. In the rare instance, unexpected activity of the combination of chemicals is obtained.

One group of chemicals which has been identified as having pesticidal activity is the avermectins. The avermectins are disaccharide derivatives of pentacyclic, 16-membered lactones. They can be divided into four major compounds: $A_{1a}$, $A_{2a}$, $B_{1a}$, and $B_{2a}$; and four minor compounds: $A_{1b}$, $A_{2b}$, $B_{1b}$, and $B_{2b}$. The a and b series are sec-butyl and isopropyl homologues, respectively, which generally have similar biological activity. Despite the structural similarities to some antibiotic materials, the avermectins are believed to be devoid of antibacterial or antifungal properties.

The organism which produces avermectins was isolated and identified as *Streptomyces avermitilis* MA-4680 (NRRL-8165). Characteristics of the avermectin producing culture and the fermentation process are well documented and known to those skilled in the art (Burg, R. W. et al. [1979]"Avermectins, New Family of Potent Anthelmintic Agents: Producing Organism and Fermentation," Antimicrob. Agents Chemother. 15(3):361–367). The isolation and purification of these compounds is also described in U.S. Pat. No. 4,310,519, issued Jan. 12, 1982.

Another family of compounds produced by fermentation are the milbemycins, which are closely related to the avermectins. The milbemycins can be produced by a variety of Streptomyces and originally differed from the avermectins only in the C-13 position. The milbemycins and their many derivatives are also well known to those skilled in the art and are the subject of U.S. patents.

Although the avermectins were initially investigated for their anthelmintic activities, they were later found to have other insecticidal properties. There seem to be no clear boundaries of activity for the avermectins. That is, most of the compounds exhibit anthelmintic as well as insecticidal properties, although the degree varies. The activity of avermectins must generally be determined empirically.

The use of avermectins in various agricultural applications has been described in publications and patents. Specifically, the use of avermectin with spray oils (lightweight oil compositions) has been described. See, for example, U.S. Pat. No. 4,560,677 issued Dec. 24, 1985; EPO applications 0 094 779 and 0 125 155; and Anderson, T. E., J. R. Babu, R. A. Dybas, H. Mehta (1986) J. Econ. Entomol. 79:197–201.

The avermectins are reported to act by blocking neuromuscular transmission. This blockage results in immobilization of the parasite or insect. Several groups of investigators have indicated γ-amino-butyric acid (GABA) release as the target system. GABA is an inhibitory neurotransmitter in vertebrates as well as invertebrates. It has been hypothesized that the avermectins cause a specific prolonged release of GABA.

22,23-dihydroavermectin $B_1$ is a synthetic derivative of the avermectins and has been assigned the nonproprietary name of Ivermectin. It is a mixture of 80% 22,23-dihydroavermectin $B_{1a}$ and 20% 22,23-dihydroavermectin $B_{1b}$. Ivermectin has been tested on a variety of laboratory and domestic animals for control of nematodes, ticks, and heartworms. It is applied both orally and subcutaneously.

Avermectin $B_{2a}$ is active against the rootknot nematode, *Meloidogyne incognita*. It is reported to be 10–30 times as potent as commercial contact nematicides when incorporated into soil at 0.16–0.25 kg/ha (Boyce Thompson Institute for Plant Research 58th Annual Report [1981]; Putter, I. et al. [1981]"Avermectins: Novel Insecticides, Acaracides, and Nematicides from a Soil Microorganism," Experientia 37:963–964). Residual activity was noted for up to 2 months in greenhouse tests using sandy-loam soil. The residual activity is attributed to a nematicidally active metabolite derived from avermectin $B_{2a}$. The soil half-life of the metabolite is approximately one month. Nematicidal efficacy is dependent on soil-type and is least effective in organic soils. Avermectin $B_{2a}$ was not toxic to tomatoes or cucumbers at rates of up to 10 kg/ha.

Avermectin $B_1$ is a combination of avermectin $B_{1a}$ (major component) and avermectin $B_{1b}$. It has demonstrated a broad spectrum of insecticidal activities. Avermectin $B_1$ displays a slow toxic action to insects as compared to organophosphate or pyrethroid insecticides. Insects become moribund soon after contact and die 3–4 days later. In several species a paralysis is induced which limits mobility and feeding. Once applied and dried on foliage, $B_1$ is not rapidly degraded by sunlight nor washed away by rain.

The data indicate that avermectin $B_1$ is primarily a miticide, although it is also effective on the Colorado potato beetle, potato tuberworm, beet armyworm, diamondback moth, gypsy moth, and the European corn borer. Marginal activity has been found on several other species.

Use of avermectin $B_{1a}$ on the imported fire ant (*Solenopsis invicta*) has been found to permanently halt egg production in queen ants (Putter et al., supra). Death of worker ants seems to be a secondary effect which occurs more frequently at high dose rates. The mechanism by which this happens is not known.

Among the pests against which the novel compositions of the instant invention are active are mites, leafminers, whiteflies, psylla, and fire ants. These are important pests, as described below.

Feeding damage caused by the two-spotted spider mite (TSM), *Tetranychus urticae* is initially manifested as a stippling of the plant leaves and chlorophyll damage. Subsequent symptoms include a yellowing or silvering of the leaves followed by eventual defoliation. Hatching eggs pass through one larval and two nymphal stages reaching adulthood in 8–12 days. Each female may lay up to 100 eggs in her 30 day lifespan. TSM occur on the underside of leaves, making coverage difficult. Overlapping generations confer a great biotic potential to TSM, resulting in outbreaks and contributing to the development of insecticide resistance. TSM are ubiquitous in that they are found in greenhouses and on vegetables, ornamentals, and fruit.

Female leafminers, *Liriomyza trifoli*, become active at dawn, feeding on leaf juices by repeatedly puncturing the leaf surface. Males feed from the punctures made by the female. Approximately 15 % of these feeding holes are used for egg-laying. Each female can lay approximately 250 eggs in her 30 day life span. Eggs hatch in 3–5 days, with the resulting maggots causing the characteristic "mines" as they tunnel and feed throughout the leaf, reducing photosynthetic rates and leading to reduced plant growth and development. Under favorable conditions, the life cycle can be completed in three weeks or less. If left unchecked, several overlapping generations can mature to further infest the crop. The development of insecticide resistance and reduction of the associated beneficial insect complex brought on by widespread use of broad spectrum insecticides has elevated leafminers from a minor to major pest status in ornamentals and vegetables such as chrysanthemums, carnations, tomatoes, and celery. California celery growers lost approximately $20 million in the last half of 1984 due to *L. trifoli.*

Whiteflies, mites, aphids, thrips, mealybugs, and other pests cause millions of dollars of damage each year to ornamental plants and plants grown in greenhouses. For example, the sweetpotato whitefly, *Bemisia tabaci*, is widely distributed throughout tropical and subtropical areas north and south of the equator. *B. tabaci* is a primary pest of cotton, ornamentals, and vegetables, both in the field and in the greenhouse. During 1981, *B. tabaci* was responsible for crop and market losses of $100 million in cotton, cucurbits, and lettuce and California and Arizona. The whitefly is increasingly a problem in Florida where, in 1986, *B. tabaci* caused approximately $2 million of damage to Florida's $8–10 million poinsettia crop. This insect is now known to feed on more than 500 different plants, many of which are of importance in the Caribbean and Florida. For example, cassava, sweet potato, squash, tomato, beans, lettuce, cotton, pepper, carrot, cucumber, eggplant, and watermelon are all known hosts. Sweetpotato whitefly advance from the newly laid egg, through the crawler and scale-like nymphal stages, through the pupal stage, to the newly emerged adult whitefly in approximately 3–4 weeks. Whiteflies may cause direct damage at very high densities through sap removal. Indirect damage may occur through virus and mycoplasma plant disease transmission. Production of honeydew may result in sooty mold contamination. Variability in time required for development among individuals within a population, and frequent arrivals of adults from the neighboring environment, ensures populations of mixed life stages. Treating all life stages of a pest, as opposed to discrete life stages, increases the rate of resistance development, with whiteflies being no exception. *B. tabaci* (Gennadius) has proven to be very difficult to control with conventional pesticide applications. Many factors contribute to the lack of control obtained with pesticides. The most important factor is that this white fly has demonstrated a broad spectrum of resistance to chlorinated hydrocarbon, organophosphorus, carbamate, and synthetic pyrethroid insecticides. Very few commercially available pesticides are effective against whiteflies, and those which do work are only effective if care is taken to make a very thorough application of the insecticide several times a week.

The pear psylla, *Psylla pyricola,* is a primary pest in all major pear-growing areas of North America, causing leaf abscission and a reduction in fruit size, root growth, tree growth, and fruit set in years following high psylla populations. Pear psylla are characterized by a distinct summer and overwintering adult form. There may be from two generations in Ontario to as many as five in California. Applications of insecticide are currently timed to coincide with early season egg deposition or tree developmental stages such as delayed dormant, petal fall, midsummer, and post-harvest. Fruit russet from honeydew contact is the principal injury caused by pear psylla, becoming evident approximately seven days after honeydew contact with the fruit. A sooty mold usually develops in the honeydew and blackens the affected tissue. Feeding by large populations of psylla can result in "psylla shock" characterized by reduced vigor, fruit loss, and poor fruit set. Toxins in the salivary secretions interfere with food transfer in susceptible cultivars, causing "pear decline" resulting in slow or rapid death of the tree. Natural enemies alone do not exert a significant influence on psylla populations, however, a "soft" insecticidal regime in combination with these natural enemies should provide economically acceptable levels of control.

The imported fire ants (IFA), *Solenopsis invicta* and *Solenopsis richteri* were introduced into the United States in the early 1900's at the port of Mobile, Alabama. Imported fire ants displace the native ant fauna and, in many areas of the southeastern United States, have become the dominant ant species. Currently, the imported fire ant has gained notoriety primarily as a result of its painful sting and its inclination to feed on a variety of materials, including cultivated plants and underground wires. The fire ant sting is not only painful but is potentially life threatening for people who suffer from an allergic reaction to the sting. Farmers throughout the southern states have suffered large economic losses as the result of fire ant infestations. Fire ants reduce the active foraging area in pastures because animals do not forage well around fire ant nests. Fire ants may also damage plants by chewing on stems or fruits. IFA has been reported to cause serious damage in young citrus groves and in vegetable crops with high cash values. Also, these ants make it difficult to harvest some crops such as hay and citrus. Large fire ant mounds may also cause damage to agricultural equipment, especially in heavy clay soil areas. Additional economic loss has resulted from the IFA chewing on electrical wiring and telephone lines in the ground or even housed in containers above the ground.

BRIEF SUMMARY OF THE INVENTION

This invention concerns novel compositions and methods for the control of pests. Specifically, mites, whiteflies, leafminers, and other agricultural pests are effectively controlled by avermectins (and related compounds) in combination with one or more substituted (or unsubstituted) saturated (or unsaturated) fatty acids (or their salts). The fatty acids of the subject invention can be from about C7 to about C20 and can be, for example, in the epoxide, cyclopropane, methylated, or hydroxylated forms. The fatty acids of the subject invention can be represented by the following formula:

$$R_1Y_1Y_2COOR_2$$

wherein $R_1$=C6 to C19 saturated or unsaturated hydrocarbon, or an epoxide, or cyclopropane thereof $Y_1$=H, C1-C5 hydrocarbon, or hydroxyl at any position along $R_1$ $Y_2$=H, C1-C5 hydrocarbon, or hydroxyl at any position along $R_1$ $R_2$=H, or salt.

Specifically exemplified herein are saturated fatty acids of length C15 to C20 in combination with avermectin. The use of the compositions described here, when used in the proportions and application rates set forth more fully hereinafter, results in an unexpected, enhanced pesticidal effect.

The avermectin compound used according to the subject invention may be any of the avermectins, milbemycins, or derivatives of either, having activity against a target pest. The avermectin's activity will be enhanced in a synergistic manner when combined with a fatty acid as described herein. Thus, the specific combination of ingredients can be manipulated to provide the optimal composition for a particular application. It is within the skill of a person trained in this art to use the teachings presented herein to prepare appropriate compositions for use against a specific pest or in a specific application. For example, for animal health applications, ivermectin will generally be used with the fatty acid. Also, because of phytotoxicity associated with the shorter chain fatty acids, fatty acids of C15 to C20 will most commonly be used to kill pests on plants. For killing pests associated with animals, however, shorter chain fatty acids may be used. For example, in animal health applications, C7 to C15 fatty acids are advantageous.

The composition of the present invention comprises a mixture of components wherein said mixture is sufficiently active so that application of the composition enables utilization of reduced amounts of each of the active ingredients while still providing effective pest control.

Since the level of pest control obtained following application of the prescribed mixture is generally much superior to that obtained following application of either active component alone, the practice of the present invention provides a desirable economic advantage to the user. Furthermore, the reduction in the amount of chemicals introduced into the environment is an additional advantageous element of the subject invention. Advantageously, the compositions of the subject invention can provide selective pesticidal activity.

DETAILED DESCRIPTION OF THE INVENTION

The fatty acids used according to the subject invention can be unsubstituted, or substituted, saturated, or unsaturated, fatty acids (or their salts), of about C7 to about C20. Specifically exemplified are fatty acids of length C15 to C20, as typified by, but not limited to, oleic acid and metal salts of these acids. The fatty acid component of the subject invention may be a single fatty acid or salt, or a mixture of two or more fatty acids or salts thereof. Fatty acids, or their salts, which can be used according to the subject invention can be fatty acids, such as oleic acid, which are known to have pesticidal activity. When used according to the subject invention, these fatty acids, or their salts, can be used in approximately the same concentrations suggested by prior practice, however, by combining these accepted concentrations with a reduced concentration of an avermectin compound, an enhanced pesticidal activity is observed compared to the avermectin compound alone at a standard concentration. Standard concentrations of fatty acids and avermectins are well known to those skilled in the art. For example, the avermectin compounds can be employed in the synergistic combination at concentrations of from about 0.03 to about 110 parts per million (ppm). Preferably, from about 1 to about 55 ppm are employed for optimum field control of the mite population. The fatty acid component of the composition may be applied at concentrations of at least about 0.2% up to about 5.0% or more. Preferably the concentration will be about 0.5% to about 3.0%. As would be readily appreciated by a person skilled in the art, the delivery of the fatty acid and/or avermectin compound can be calculated in terms of the active ingredient applied per unit area. For example, the fatty acid may be applied at a rate of about 1 lb/acre to 70 lbs/acre and, preferably, about 3 lbs/acre to about 50 lbs/acre. Similary, the avermectin product can be applied at a rate of up to about 16 oz. of formulated product (Avid®, available from Merck) per acre. Preferrably, about 4 oz to about 8 oz formulated Avid® per acre would be used. Thus, the avermectin compound can be applied up to about 0.02 lbs/acre. Preferrably, the rate of avermectin is between about 0.005 lbs/acre and 0.01 lbs/acre. A person of ordinary skill in the art would readily appreciate that the desired application rate of the active ingredients could be achieved using a great variety of different concentrations of active ingredients while varying the application rate of the solution. Thus, a large quantity of dilute solution could be applied or a smaller quantity of a more concentrated solution.

A variety of different avermectins or related compounds can be used alone or in combination according to the subject invention. Ivermectin may also be used according to the subject invention, as may the milbemycins. For brevity, the term "avermectin" is used herein to refer to all the avermectins and their derivatives as well as related compounds such as the milbemycins and the ivermectins. "Derivatives" refer to chemical modifications of the avermectins or milbemycins which are well known and available to those skilled in this art. Such derivatives are described, for example, in U.S. Pat. No. 4,560,677.

In using the compounds of this invention, the individual avermectin components may be prepared and used in that form. Alternatively, mixtures of two or more of the individual avermectin components may be used, as well as mixtures of the parent avermectin compounds, other avermectin compounds, or other active compounds not related to the avermectins and the compounds of the invention.

One embodiment of the present invention consists of the application of a tankmix of a fatty acid and an avermectin. A further embodiment contemplates sequential application of a fatty acid and an avermectin.

Tank mixes of fatty acids and avermectins can be prepared according to procedures which are well known to those skilled in the art. For example, The avermectin and the fatty acid agricultural spray oil combination can be prepared using a solvent solution or emulsion of the avermectin compound or compounds, the fatty acid, a surfactant, and sufficient water to dilute the mixture to the desired concentration.

The surfactants which may be used to emulsify the fatty acid and the avermectin in the aqueous formulations are any of the non-phytotoxic surfactants, which are customarily used in preparing formulations for use on agricultural crops. The composition of the subject invention may also be combined with a spray oil as described in U.S. Pat. No. 4,560,677.

Avermectin is readily available under a variety of tradenames including AVID®, ZEPHYR®, VERTIMEC®, and AGRI-MEK®. Fatty acids which can be used according to the subject invention are also widely available and are sold under a variety of tradenames including M-PEDE® and SAFER® Insecticide Concentrate (SIC).

The compositions of the subject invention can be used against a variety of pests including, but not limited to, the following families of mites:

Tetranychidae: Examples: *Tetranychus urticae* (two-spotted mite), *T. pacificus* (Pacific mite), *T. mcdanieli* (McDaniel mite), *T. turkestani* (strawberry mite), *Panonychus ulni* (European red mite), *P. citri* (citrus red mite), *Oligonychus pratensis* (Banks grass mite), *O. punicae* (avocado brown mite), *Eutetranychus hicoriae* (pecan leaf scorch mite), *Byrobia praetiosa* (clover mite).

Eriophyidae (rust and blister mites): Examples: *Phyllocoptruta oleivora* (citrus rust mite), *Eriophyes sheldoni* (citrus bud mite), *E. erinea* (walnut blister mite), *Epitrimerus pyri* (pear rust mite), *Aculops lycopersici* (tomato russet mite).

Tenuipalpidae: Examples: *Brevipalpus lewisi* (citrus flat mite), *B. phoenicis* (red and black flat mite), *Dolichotetranychus floridanus* (pineapple false spider mite).

Tarsenomidae: Examples: *Steneotarsonemus bancrofti* (sugarcane stalk mite), *S. ananas* (pineapple tarsenomid), *S. pallidus* (cyclamen mite), *Acarapis woodi* (honeybee mite).

The compositions can also be used against the following families of sucking insects:

Aleyrodidae (whiteflies): Examples: *Bemisia tabaci* (sweetpotato whitefly), *Trialeurodes vaporariorum* (greenhouse whitefly), *Siphoninus phillyreae* (ash whitefly), *Dialeurodes citrifolii* (cloudywinged whitefly), *Aleurocanthus woglumi* (citrus blackfly).

Psyllidae (psyllids): Examples: *Psylla pyricol* (pear psylla), *Paratrioza cockerelli* (potato/tomato psyllid).

The compositions can also be used against leaf mining flies of the order Diptera and family Agromyzidae. Examples of these flies are *Liriomyza complex* (serpentine leafminers), *Phytomyza syngenesiae* (chrysanthemum leafminer), *Agromyza frontella* (alfalfa blotch leafminer), *Ophiomyia phaseoli* (bean fly).

Other target pests include, but are not limited to, Thysanoptera (thrips), Hymenoptera (wasps), Hemiptera (bugs), Cicadellidae (leafhoppers), Membracidae (treehoppers), Coccidae (scales), Pseudococcidae (mealybugs), Diaspididae (scales), and Solenopsis (fire ants).

The compositions of the subject invention can also be used in animal health applications to kill pests on livestock and on pets. As used herein, "livestock" can refer to, for example, cattle, pigs, sheep, chicken, and turkeys. "Pets" can refer to, for example, dogs, cats, horses, and rabbits. For this use the composition can be formulated into a drench (pourable) product. The pests controlled by such a composition could include, for example, fleas (order Siphonaptera), family Pulicidae; ticks (order Acari), families Ixodidae and Argasidae; mites (order Acari), families Sarcoptidae, Dermanyssidae, Demodicidae, Macronyssidae, Psoroptidae; lice (order Anoplura), families Haematopinidae, Linognathidae, Pediculidae, Hoplopleuridae; lice (order Mallophaga), families Trichodectidae, Philopteridae; flies (order Diptera), families Calliphoridae, Gastrophilidae, Hippoboscidae, Oestridae.

Following are examples which illustrate procedures, including the best mode, for practicing the invention. These examples should not be construed as limiting. All percentages are by weight and all solvent mixture proportions are by volume unless otherwise noted.

EXAMPLE 1

Control of Sweetpotato Whitefly on Head Lettuce

A small plot trial was conducted on head lettuce to compare the efficacy of M-PEDE® (fatty acids), AVID® (avermectin), and reduced-rate tank-mix combinations of these compositions for control of adult sweetpotato whitefly (*Bemesia tabaci*). It was determined that combinations of M-PEDE® with AVID® gave better control than AVID® treatments alone.

Single bed double-row lettuce treatments, consisting of 30 foot plots separated by 5 foot alleyways were replicated four times in a randomized complete block experimental design with treatment beds separated by an untreated bed. Insecticides were applied with a $CO_2$-powered backpack sprayer operating at 70 PSI and delivering 81 GPA through two hollow cone nozzles (TX10, Spraying Systems Co.) arranged as drops to cover each plant from the sides with a 12 inch effective swath width. Each row (2 per bed) was treated separately up and back in each treatment plot and Nufilm-P (3.0 oz./A) was added to all treatments. Insect counts were taken at 2 hours, 4 hours, and 4 days post treatment and consisted of suction samples of the treated plants. Suction samples using a modified DUSTBUSTER® equipped with a 80 dram plastic vial (Thornton Plastic Co.) with a screened bottom, were taken from 10 consecutive lettuce plants for a duration of 2 seconds/plant (20 seconds/plot). Plants were agitated by hand while suction was applied and an effort was made to capture all disturbed whiteflies. Whitefly totals/vial were counted 24 hours later and treatment averages determined across all four replicate plots (Table 1).

It is readily apparent from Table 1 that the combination of M-PEDE® (fatty acids) with AVID® (avermectin) greatly improved the amount of whitefly control compared to AVID® alone. Even when AVID® was used at a concentration of only 4 oz. (with 1% M-PEDE®), the level of control (73%) was greater than the level of control achieved for 12.0 oz. AVID®.

TABLE 1

Control of adult sweetpotato whitefly on lettuce with reduced-rate tank-mixes of M-PEDE ® and AVID ®

| Treatment | Rate/A | Av. Adult Whiteflies/10 plants | | | | Percent Control[1] |
|---|---|---|---|---|---|---|
| | | 2 hrs* | 4 hrs* | 4 days* | Av. total | |
| Thiodan | 1 qt. | 16.3 | 8.5 | 3.5 | 9.4 | 80.0 |
| Thiodan | 0.5 qt. | 21.8 | 9.8 | 5.3 | 12.3 | 73.8 |
| AVID ® | 12.0 oz. | 14.8 | 18.8 | 7.0 | 13.5 | 71.3 |
| AVID ® | 4.0 oz. | 25.3 | 24.5 | 7.0 | 18.9 | 59.8 |
| Thiodan + AVID ® | 0.5 qt. + 4.0 oz. | 24.3 | 9.0 | 4.0 | 12.4 | 73.6 |
| M-PEDE ® + Thiodan | 1% + 0.5 qt. | 21.0 | 6.8 | 3.8 | 10.5 | 78.0 |
| M-PEDE ® + AVID ® | 1% + 4.0 oz. | 21.8 | 12.5 | 3.8 | 12.7 | 73.0 |

[1]Percent Control calculated as: ((Average Whiteflies Treatment - Average Whiteflies Control) ÷ Average Whiteflies Control) × 100.
*Sampled hours or days post treatment as suction sample from 10 plants/2 sec/plant.

EXAMPLE 2

Efficacy of Fatty Acid Combined with Avermectin Composition for Control of Mites Safer, Inc. miticide formulations were tested in combination with AVID ® 0.15EC (avermectin composition) and compared to AVID ® 0.15EC alone for control of the twospotted spider mite (TSM), *Tetranychus urticae*, Koch in winter planted strawberries (cv. Selva) with predatory mites, *Phytoseiulus persimilis*. Recently, California strawberry growers have implemented the use of predatory mites, *P. persimilis*, to assist in TSM control. The purpose of the experiment was to evaluate the efficacy of NSIS-50C (fatty acids) combined at rates of 1.3 fl. oz./gal. with lower than standard rates of AVID ® 0.15EC, compared to AVID ® 0.15EC alone (at standard rate) for control of the TSM and to evaluate the toxicity of these treatments to the predatory mite, *P. persimilis*. Each of the treatments was evaluated for its influence on fruit flavor.

Materials and Methods

The trial was conducted with the Selva strawberry variety at Kando Berry Farms in Salinas, Monterey County, Calif. The strawberry plants were transplanted in November and the trial was initiated with five treatments in April. A detailed description of each treatment follows:

1. AVID ® 0.15EC at 0.064 fl. oz./gal.
2. NSIS-50C at 1.3 fl. oz./gal. plus AVID ® 0.15EC at 0.032 fl. oz./gal.
3. NSIS-50C at 1.3 fl. oz./gal. plus AVID ® 0.15EC at 0.016 fl. oz./gal.
4. NSIS-50C at 1.3 fl. oz./gal. plus AVID ® 0.15EC at 0.008 fl. oz./gal.
5. Untreated check-water.

Each of the five treatments was replicated four times in a randomized complete block design. Each replicate consisted of 20 feet of raised bed on 48 inch centers, with two rows of plants per bed.

Twospotted spider mite and predatory mite populations (motiles and eggs) within each treatment were determined by randomly selecting 10 mature leaflets per replicate (total of 40 leaflets per treatment) and brushing them through a Llanfair mite brushing machine. All TSM and *P. persimilis* motiles and eggs were brushed off of the leaves onto a glass plate coated with a thin film of liquid detergent (to which the motiles and eggs adhere). Each glass plate was then placed over a twenty sectored counting template, and the motiles and eggs of each mite species counted under a binocular microscope.

Five applications of each treatment were made at 14-day intervals beginning on April 29. The first two applications were made as full coverage sprays while the final three sprays were made as "over the top" sprays. Immediately prior to the first application, a pretreatment count was taken. Post treatment counts of TSM and predatory mite populations were made at seven day intervals following the first application for a total of thirteen counts.

Fruit flavor was also evaluated in each treatment three days after the third and fourth applications. One single pint basket of fruit per treatment (two baskets from the untreated check) was harvested for each flavor evaluation. The fruit from each treatment was capped, quartered from top to bottom, and placed on a separate sample plate with the treatment labeled on the underside (unseen by flavor testing panel). Sample plates were then randomly arranged and numbered. The second pint basket of untreated check fruit was prepared in the same manner and labeled conspicuously as the "known check fruit." A taste panel of four persons rated the fruit on a scale of 0–5 (0=very poor or off flavor; 5=excellent flavor) comparing fruit from each plate (treatment) with the known check fruit.

Results

A. Twospotted Spider Mite Populations. Pretreatment (0-day) counts in the test plots averages 11.5 motiles and 49.6 eggs per leaflet. Post treatment counts taken from 7–49 days after the first application of miticide treatments show a distinct rate response from the addition of a constant rate of NSIS-50C (1.3 fl. oz./gal,) to decreasing rates of AVID ® 0.15EC (0.032, 0.016, and 0.008 fl. oz./gal.). The NSIS-50C/AVID ® 0.15EC (0.032 fl. oz./gal.) combination treatment provided greater TSM (motile and egg) control than AVID ® 0.15EC alone at 0.064 fl. oz./gal. The NSIS-50C/AVID ® 0.15EC (0.016 fl. oz./gal.) combination treatment provided comparable TSM control compared to AVID ® 0.15EC alone at 0.064 fl. oz./gal. while the addition of NSIS-50C to the 0.008 fl. oz./gal. rate of AVID ® 0.15EC provided less TSM control than AVID ® 0.15EC alone at the standard rate of 0.064 fl. oz./gal.

The TSM populations in the five treatments were not being influenced by predatory mites from the 7-day through the 35-day TSM evaluations. The predatory mites (30,000/acre) which were initially released into the test plot were killed off by the first two full coverage miticide applications. By 42 days after the first application (14 days after the third miticide applications-applied as top coverage sprays only), the TSM population in the UTC began to drop, as predatory mites became established in the test plot.

B. Predatory Mite Populations. Four days prior to the first application and three days after the third application the equivalent of 30,000 predatory mites (*Phytoseiulus persimilis*) per acre were released into the test plot for a total predator population equivalent to 60,000 per acre. The first release of predators were killed off by the first two full-coverage miticide applications. Predatory mite populations became reestablished in all treatments by the 42 day evaluation, after the second release of 30,000 per acre. By fourteen days after the final (5th) application, predatory mites were found in all treatments. Predatory mite populations fell at or below 0.1 motile plus egg per leaflet in all miticide treatments for the remainder of the test. These predatory mites most likely moved out into heavier TSM infested areas of the field after the TSM population dropped to less than 1.0 motile plus egg per leaflet in all treatments of the test plot.

C. Fruit Flavor. The mean flavor ratings given to all treatments from flavor tests conducted one day after both the third and fourth applications were found to be statistically equal.

Discussion

The results from this field trial indicate that the treatments tested, when applied as full coverage sprays (equivalent to 250 gallons of water per acre), are highly toxic to the predatory mite, P. persimilis, as well as to TSM. The first two miticide applications were applied as full coverage sprays, eliminating the predatory mites which were released into the plot prior to initiation. The combination of NSIS-50C at 1.3 fl. oz./gal. plus AVID ® 0.15EC at 0.032 fl. oz./gal. (half the standard rate) provided approximately twice the control of TSM over AVID ® 0.15EC applied alone at 0.064 fl. oz./gal. The combination of NSIS-50C at 1.3 fl. oz./gal. plus AVID ® 0.15 EC at 0.016 fl. oz./gal. (one quarter the standard rate) provided TSM control comparable to AVID ® 0.15EC alone (0.064 fl. oz./gal.) while the lowest rate of AVID ® 0.15EC (0.008 fl. oz./gal.) combined with NSIS (1.3 fl. oz./gal.) provided less TSM control than AVID ® 0.15EC alone at 0.064 f. oz./gal. These results are summarized in Table 2.

The final three miticide applications of treatments 1-5 as "over the top" sprays at the equivalent of 50 gallons of water per acre allowed the predatory mite to become reestablished. These applications were shown to be less effective than full coverage sprays in controlling TSM, as counts increased seven days after the third application (first application, over the top) in all miticide treatments. However, as these TSM populations were increasing, the predatory mite populations were also on the increase. Fourteen days after the third application, increasing predator populations reduced TSM populations in all treatments, including the UTC. The predator mites dropped TSM counts to less than 1.0 motile plus egg per leaflet by the 56-day count and held the TSM populations at this level for the remainder of the test.

TABLE 2

Control of two-spotted spider mite (Tetranychus urticae) motiles on strawberries with reduced tank rate mixed of AVID ® 0.15EC plus M-PEDE ®.

| Treatment | Rate/A | % Control of TSM 2 weeks after each spray application[1] | | | | | |
|---|---|---|---|---|---|---|---|
| | | 5/13 | 5/27 | 6/10 | 6/24 | 7/8 | 7/22 |
| AVID ® | 16 oz. | 62 | 88 | 93 | 94 | 84 | 78 |
| M-PEDE ® AVID ® | 1% v/v 8 oz. | 84 | 87 | 95 | 99 | 99 | 99 |
| M-PEDE ® AVID ® | 1% v/v 4 oz. | 58 | 64 | 92 | 95 | 97 | 98 |
| M-PEDE ® AVID ® | 1% v/v 2 oz. | 72 | 66 | 80 | 76 | 46 | 60 |

[1]% Control = {[Average # TSM (Treatment) − Average # TSM (Control)] ÷ Average # TSM (Control)} × 100

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. A composition for the control of a pest, said composition comprising a first ingredient which is a monocarboxylic acid having about seven to about twenty carbon atoms, or a salt thereof, or a mixture of said monocarboxylic acids or salts thereof, and a second ingredient which is an avermectin, ivermectin, or milbemycin, wherein said first ingredient is present in a concentration of at least about 0.2% and the second ingredient is present in a concentration between about 3 ppm and about 110 ppm.

2. The composition, according to claim 1, wherein said first ingredient can be represented by the following formula:

$$R_1 Y_1 Y_2 COOR_2$$

wherein $R_1$ = C6 to C19 saturated or unsaturated hydrocarbon, or an epoxide, or cyclopropane thereof $Y_1$ = H, C1-C5 hydrocarbon, or hydroxyl at any position along $R_1$ $Y_2$ = H, C1-C5 hydrocarbon, or hydroxyl at any position along $R_1$ $R_2$ = H, or salt.

3. The composition, according to claim 1, wherein said first ingredient has from about fifteen to about twenty carbons.

4. The composition, according to claim 1, wherein said first ingredient is a mixture of monocarboxylic acids or salts thereof.

5. The composition, according to claim 1, wherein said first ingredient is saturated and unsubstituted.

6. The composition, according to claim 1, wherein said first ingredient is oleic acid or a salt thereof.

7. The composition, according to claim 1, wherein said second ingredient is an avermectin.

8. The composition, according to claim 1, wherein said second ingredient is a milbemycin.

9. The composition, according to claim 1, wherein said second ingredient is an ivermectin.

10. The composition, according to claim 1, wherein said composition is formulated to be a drench product to be applied to livestock or pets.

11. The composition, according to claim 10, wherein said first ingredient has from about seven to about eighteen carbons.

12. The composition, according to claim 11, wherein said first ingredient is decanoic or nonanoic acid or salts thereof.

13. The composition, according to claim 1, wherein said first ingredient is a metal salt of a monocarboxylic acid.

14. A method for the control of a pest, said method comprising the administration to said pest of an effective amount of a composition comprising a first ingredient which is a monocarboxylic acid having about seven to about twenty carbons, or a salt thereof, or a mixture of monocarboxylic acids or salts thereof, and a second ingredient which is an avermectin, ivermectin, or milbemycin, wherein said first ingredient is applied at a rate of at least about 1 lb/acre, and said second ingredient is applied at a rate of about 0.0006 lbs/acre to about 0.02 lbs/acre.

15. The method, according to claim 14, wherein said first ingredient can be represented by the following formula:

$$R_1 Y_1 Y_2 COOR_2$$

wherein
- $R_1$ = C6 to C19 saturated or unsaturated hydrocarbon, or an epoxide, or cyclopropane thereof
- $Y_1$ = H, C1–C5 hydrocarbon, or hydroxyl at any position along $R_1$
- $Y_2$ = H, C1–C5 hydrocarbon, or hydroxyl at any position along $R_1$
- $R_2$ = H, or salt.

16. The method, according to claim 14, wherein said first ingredient has from about fifteen to about twenty carbons.

17. The method, according to claim 14, wherein said first ingredient is oleic acid or a salt thereof.

18. The method, according to claim 14, wherein said second ingredient is an avermectin.

19. The method, according to claim 14, wherein said second ingredient is a milbemycin.

20. The method, according to claim 14, wherein said second ingredient is ivermectin.

21. The method, according to claim 14, wherein said composition is formulated to be a drench product to be applied to livestock or pets.

22. The method, according to claim 14, wherein said first ingredient has from about seven to about eighteen carbons.

23. The method, according to claim 14, wherein said first ingredient is a metal salt of a monocarboxylic acid.

24. The method, according to claim 14, wherein said pest is in a taxonomic family selected from the group consisting of Tetranychidae, Eriophyidae, Tenuipalpidae, Tarsenomidae, Aleyrodidae, Psyllidae, Agromyzidae, Cicadellidae, Membracidae, Coccidae, Pseudococcidae, and Diaspididae.

25. The method, according to claim 14, wherein said pest is selected from the group consisting of Thysanoptera, Hymenoptera, Hemiptera, Cicadellidae, Membracidae, Coccidae, Pseudococcidae, Diaspididae, and Solenopsis.

26. The method, according to claim 14, wherein said pest is selected from the group consisting of mites and whiteflies.

27. The method, according to claim 21, wherein said pest is selected from the group consisting of fleas, ticks, mites, lice, and flies.

28. A method for the control of a pest, said method comprising the sequential application to said pest of a first composition comprising a monocarboxylic acid having about seven to about twenty carbon atoms, or a salt thereof, or a mixture of monocarboxylic acids or salts thereof, and a second composition comprising avermectin, ivermectin, or milbemycin wherein said first ingredient is present in a concentration of at least about 0.2% and the second ingredient is present in a concentration between about 3 ppm and about 110 ppm.

29. The method, according to claim 28, wherein said monocarboxylic acid can be represented by the following formula:

$$R_1 Y_1 Y_2 COOR_2$$

wherein
- $R_1$ = C6 to C19 saturated or unsaturated hydrocarbon, or an epoxide, or cyclopropane thereof
- $Y_1$ = H, C1–C5 hydrocarbon, or hydroxyl at any position along $R_1$
- $Y_2$ = H, C1–C5 hydrocarbon, or hydroxyl at any position along $R_1$
- $R_2$ = H, or salt.

30. The method, according to claim 28, wherein said monocarboxylic acid is oleic acid or a salt thereof.

* * * * *

UNITED STATES PATENT AND TRADEMARK OFFICE
CERTIFICATE OF CORRECTION

PATENT NO. : 5,346,698

DATED : September 13, 1994

INVENTOR(S) : Kenneth D. Abercrombie

It is certified that error appears in the above-indentified patent and that said Letters Patent is hereby corrected as shown below:

Column 11, line 32: Delete "0.064 f. oz./gal." and insert --0.064 fl. oz./gal.--

Column 11, line 52 (Table 2): Delete "rate mixed of" and insert --rate mixes of--.

Signed and Sealed this

Sixth Day of December, 1994

Attest:

BRUCE LEHMAN

*Attesting Officer*   *Commissioner of Patents and Trademarks*